(12) United States Patent
Coutard et al.

(10) Patent No.: US 10,049,453 B2
(45) Date of Patent: Aug. 14, 2018

(54) METHOD FOR ESTIMATING AN AMOUNT OF ANALYTE IN A FLUID

(71) Applicant: COMMISSARIAT A L'ENERGIE ATOMIQUE ET AUX ENERGIES ALTERNATIVES, Paris (FR)

(72) Inventors: Jean-Guillaume Coutard, Saint-Pancrasse (FR); Patrick Pouteau, Meylan (FR); Myriam Laure Cubizolles, Corenc (FR)

(73) Assignees: COMMISSARIAT A L'ENERGIE ATOMIQUE ET AUX ENERGIES ALTERNATIVES, Paris (FR); AVALUN, Grenoble (FR)

( * ) Notice: Subject to any disclaimer, the term of this patent is extended or adjusted under 35 U.S.C. 154(b) by 25 days.

(21) Appl. No.: 15/204,300

(22) Filed: Jul. 7, 2016

(65) Prior Publication Data

US 2017/0011517 A1 Jan. 12, 2017

(30) Foreign Application Priority Data

Jul. 7, 2015 (FR) ...................................... 15 56445

(51) Int. Cl.
*G06K 9/00* (2006.01)
*G06T 7/00* (2017.01)
(Continued)

(52) U.S. Cl.
CPC ........... *G06T 7/0016* (2013.01); *G01N 21/78* (2013.01); *G01N 33/49* (2013.01); *G06T 7/60* (2013.01);
(Continued)

(58) Field of Classification Search
CPC ....... G01N 33/54386; G01N 33/54366; G01N 33/5302; G01N 33/558; Y10T 436/10
(Continued)

(56) References Cited

U.S. PATENT DOCUMENTS

| 2005/0089993 A1* | 4/2005 | Boccazzi | ............ B01F 13/0059 435/286.2 |
| 2007/0116600 A1* | 5/2007 | Kochar | .................. G01N 21/76 422/65 |

(Continued)

FOREIGN PATENT DOCUMENTS

| WO | WO 2013/071301 A1 | 5/2013 |
| WO | WO 2014/068003 A1 | 5/2014 |

OTHER PUBLICATIONS

French Preliminary Search Report (with Written Opinion) dated Jun. 6, 2016 in French Application 15 56445 filed on Jul. 7, 2015 (with English Translation of Categories of Cited Documents).
Nevine Demitri, et al., "Detection of Faulty Glucose Measurements Using Texture Analysis", 22$^{nd}$ Signal Processing Conference, 2014, 5 pgs.

*Primary Examiner* — Charlotte M Baker
(74) *Attorney, Agent, or Firm* — Oblon, McClelland, Maier & Neustadt, L.L.P.

(57) ABSTRACT

The invention is a method for estimating the amount of analyte in a fluid sample, and in particular in a bodily fluid. The sample is mixed with a reagent able to form a color indicator in the presence of the analyte. The sample is then illuminated by a light beam produced by a light source; an image sensor forms an image of the beam transmitted by the sample, from which image a concentration of the analyte in the fluid is estimated. The method is intended to be implemented in compact analyzing systems. One targeted application is the determination of the glucose concentration in blood.

19 Claims, 13 Drawing Sheets

(51) Int. Cl.
*G01N 33/49* (2006.01)
*G01N 21/78* (2006.01)
*G06T 7/60* (2017.01)
*G01N 21/77* (2006.01)

(52) U.S. Cl.
CPC ............... *G01N 2021/7773* (2013.01); *G01N 2021/7783* (2013.01)

(58) Field of Classification Search
USPC ......... 382/128, 129, 133; 600/365; 250/239, 250/208.1; 257/E31.118; 435/297.5, 435/287.5, 288.7, 294.1, 303.1, 808, 809, 435/5; 356/369; 359/540, 581, 585; 422/504
See application file for complete search history.

(56) References Cited

U.S. PATENT DOCUMENTS

| | | | |
|---|---|---|---|
| 2009/0298191 A1* | 12/2009 | Whitesides | G01N 33/523 436/164 |
| 2013/0126712 A1* | 5/2013 | Petrich | G01N 21/8483 250/208.1 |
| 2013/0303869 A1* | 11/2013 | Rebec | A61B 5/14532 600/365 |
| 2014/0295472 A1 | 10/2014 | Shevkoplyas et al. | |
| 2015/0160244 A1* | 6/2015 | Huet | G01N 33/80 435/5 |
| 2015/0281609 A1 | 10/2015 | Poher et al. | |
| 2016/0076993 A1 | 3/2016 | Petrich et al. | |
| 2016/0346781 A1* | 12/2016 | Shen | G01N 1/405 |

* cited by examiner

A technical field of the invention is the analysis of bodily fluids, in particular blood, to determine an amount of an analyte, by an optical method. One application is the measurement of blood sugar level.

METHOD FOR ESTIMATING AN AMOUNT OF ANALYTE IN A FLUID

TECHNICAL FIELD

The technical field of the invention is the analysis of bodily fluids, in particular blood, to determine an amount of an analyte, by an optical method. One application is the measurement of blood sugar level.

PRIOR ART

The measurement of blood sugar level is a measurement commonly carried out using portable measuring devices, which are usable at home, in what are called "point of care" applications.

Blood sugar level may be measured by an optical method. This is for example the case for the device described in U.S. Pat. No. 5,866,349. In this patent, an optical method for determining whole-blood glucose concentration is described. After a hemolysis step, the method implements an enzyme reaction leading to the formation of a color indicator from a tetrazolium salt.

An image sensor measures the intensity of light transmitted by a blood sample, the latter being successively illuminated by two light-emitting diodes. A first light-emitting diode emits a first light beam at a wavelength of 660 nm, this wavelength being comprised in the absorption spectral band of the color indicator. A second light-emitting diode emits a second light beam at a wavelength comprised between 740 nm and 940 nm, in which spectral band blood has a high transmittance. A comparison of the intensity transmitted, at these two wavelengths, allows an amount of color indicator formed in the sample to be estimated, from which amount a glucose concentration may be determined.

However, this method requires the analyzed blood sample to be successively illuminated by two different light sources. It is therefore necessary for the analyzing device to comprise two light sources.

Patent EP1875203 describes a device allowing an amount of glucose in a blood sample to be estimated without implementing a hemolysis step. The measuring principle is also based on the formation of a color indicator obtained by reducing a tetrazolium salt. The blood sample is coupled to the image sensor by two lenses, which are placed in succession between the sample and the image sensor. These lenses allow the signal collected by the image sensor to be increased. The image sensor may be a CCD image sensor. Just as in U.S. Pat. No. 5,866,349, two light sources are used, one emitting in an absorption spectral band of the color indicator, the other emitting in the near infrared. The detection of the light transmitted by the sample when it is illuminated in the infrared allows a hematocrit level to be estimated; the detection of the light transmitted by the sample in the absorption spectral band of the indicator allows an amount of glucose to be estimated, this estimation being corrected for the previously determined hematocrit level. However, the use of a complex optical system based on two hemispherical lenses has an adverse effect on the compactness of the device and its cost.

Patent application US2013/0126712 describes a device for quantifying the amount of an analyte, such as glucose, in a sample, based on the intensity of pixels of an image of the sample.

The present invention is a simple and reliable method allowing glucose, or another analyte, to be quantified by way of an enzyme reaction resulting in the formation of a color indicator. This method does not require the sample to be illuminated by two light beams in two different spectral bands. In addition, it may be implemented using a simple and compact optical device.

SUMMARY OF THE INVENTION

An object of the invention is a method according to any of the attached claims. Basically, an object of the invention is a method for estimating an amount of an analyte in a fluid sample containing particles, the method including the following steps:
 a) mixing the sample with a first reagent able to form a color indicator in the presence of said analyte, in the sample,
 b) following this mixing, illuminating the sample using a light source able to emit light toward the sample,
 c) acquiring, using an image sensor, an image of light transmitted or reflected by the sample,
 d) estimating, depending on said image, an amount of said analyte from the image acquired in step c).
According to an embodiment, step d) includes the following substeps:
 i) selecting a measuring zone in said image, said measuring zone comprising a plurality of pixels,
 ii) determining, inside the measuring zone, a region of interest and at least one region of exclusion,
 iii) estimating the amount of analyte from a quantity representative of the intensity of the pixels in said region of interest, without taking into account the intensity of the pixels of each region of exclusion,
the method also including mixing the sample with a second reagent, referred to as the lysis reagent, able to lyse said particles, each region of exclusion corresponding to the trace of an air bubble, said air bubble being formed following the lysis of said particles.

The invention makes it possible not to take into account, in step d), portions of the image that are not representative of the formation of the color indicator. Moreover, the fact that an estimate is made based on an image makes it possible to take into account possible spatial variations in the quantity of analyte or in the formation of color indicator. By virtue of the invention, the estimation of the amount of analyte does not take into account the presence of these air bubbles.

In particular, in the measuring zone the region of interest is complementary to each determined region of exclusion. This makes it possible to estimate the amount of analyte over the entirety of the measuring zone, excluding the determined region or regions of exclusion. The area of the region of interest on the basis of which the estimation is made is thus maximized.

The substep ii) may especially comprise determining a plurality of regions of exclusion, which are separate and distant from one another, the region of interest extending between these regions of exclusion. Each region of exclusion may in particular be bounded by a closed annular or polygonal outline.

According to an embodiment, the method includes in step d):
 determining a lysis indicator from the image acquired in step c);
 estimating the amount of the analyte when the lysis indicator meets a preset lysis criterion.
According to this embodiment, as long as the lysis indicator does not meet a lysis criterion, step c) is reiterated in such a way that a plurality of lysis indicators are determined from images acquired at various times.

Each lysis indicator may especially be determined by forming a comparative image representing a comparison between two images acquired at different times ($t_i$, $t_{i-1}$) in particular taking the form of a difference. The lysis indicator may then be obtained from a statistical quantity of each image, or each comparative image, the statistical quantity for example being a mean, a median or a measure of dispersion such as variance or standard deviation. This makes it possible to follow the progression of the lysis using the image, and to detect the time from which the amount of analyte may be estimated.

The sample may be placed facing the light source and the image sensor, in such way that the image sensor detects radiation reflected or backscattered by the sample, the image acquired by the image sensor then being what is called a reflected image. This is more particularly relevant for thick samples, for which a transmission configuration would lead to too high an attenuation of the light transmitted by the sample.

Another object of the invention is device for estimating the amount of an analyte in a fluid sample, the device comprising:
- a light source able to emit light in the direction of said sample,
- a holder for holding the sample between said light source and an image sensor,
- the image sensor being arranged to acquire an image of the radiation transmitted or reflected by the sample when the latter is exposed to said light, and
- a processor able to estimate an amount of analyte in the sample, said processor being able to implement step d) of the method that is the subject matter of claim 1 a processor able to estimate an amount of analyte in the sample, said processor being able to implement step d) of the method herein described.

FIGURES

Figure 8A:
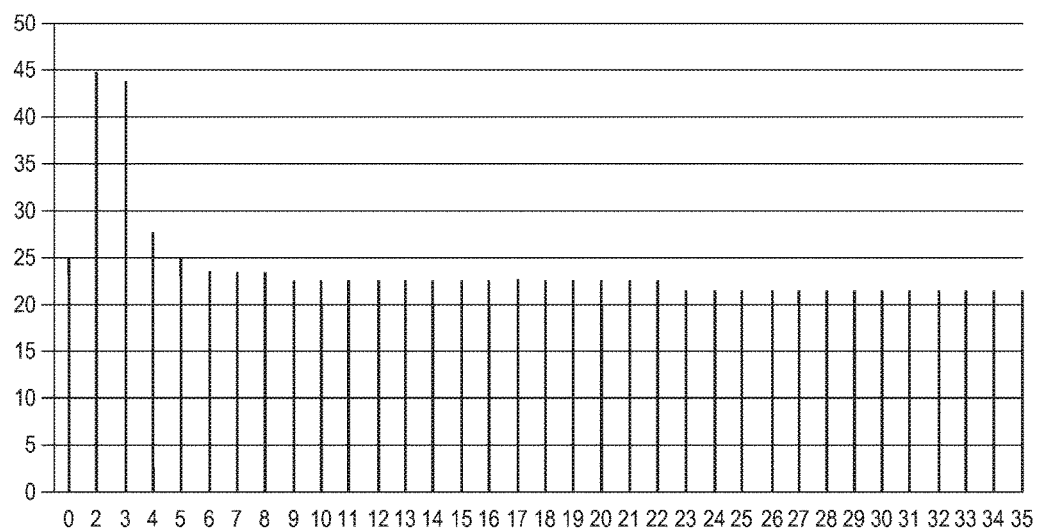
Figure 8B:
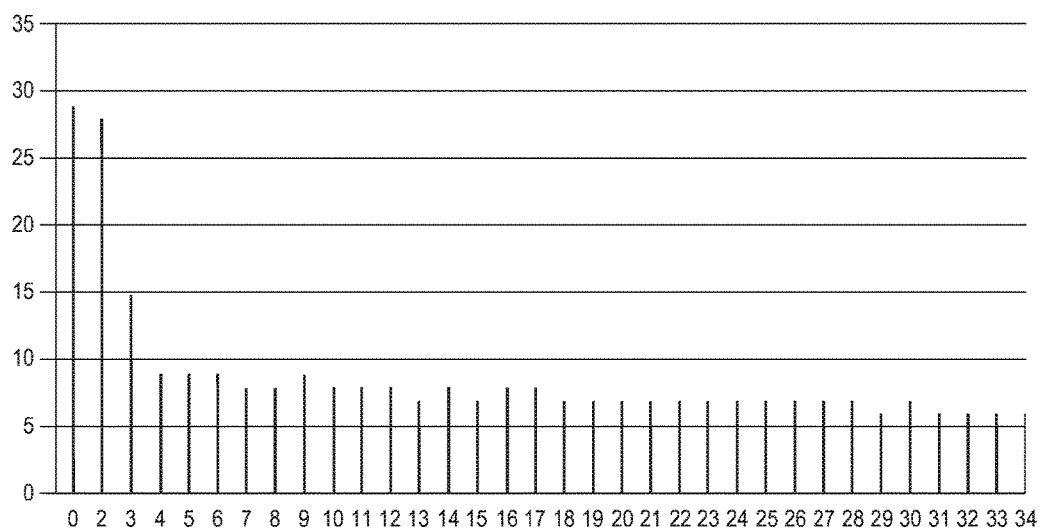
Figure 8C:
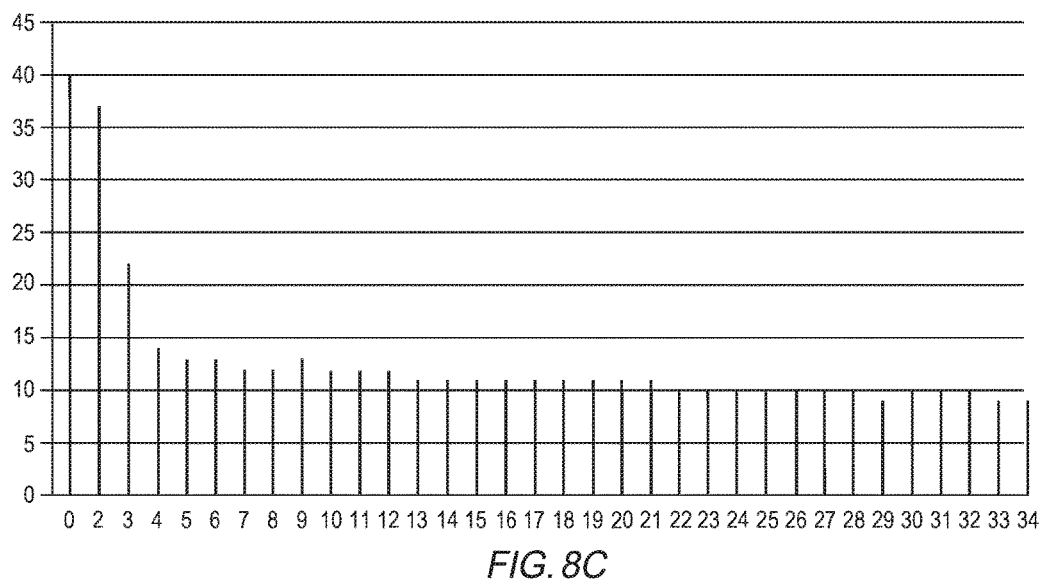

FIGS. 8A, 8B and 8C show, from images obtained using a sample having a glucose concentration of 4.8 mM, the variation in an indicator, called the lysis indicator, as a function of time. This lysis indicator is respectively the standard deviation of the intensity in each image, the mean of the intensity of a comparative image formed by finding the difference between two successive images, and the standard deviation of the intensity in said comparative image.

Figure 9A:
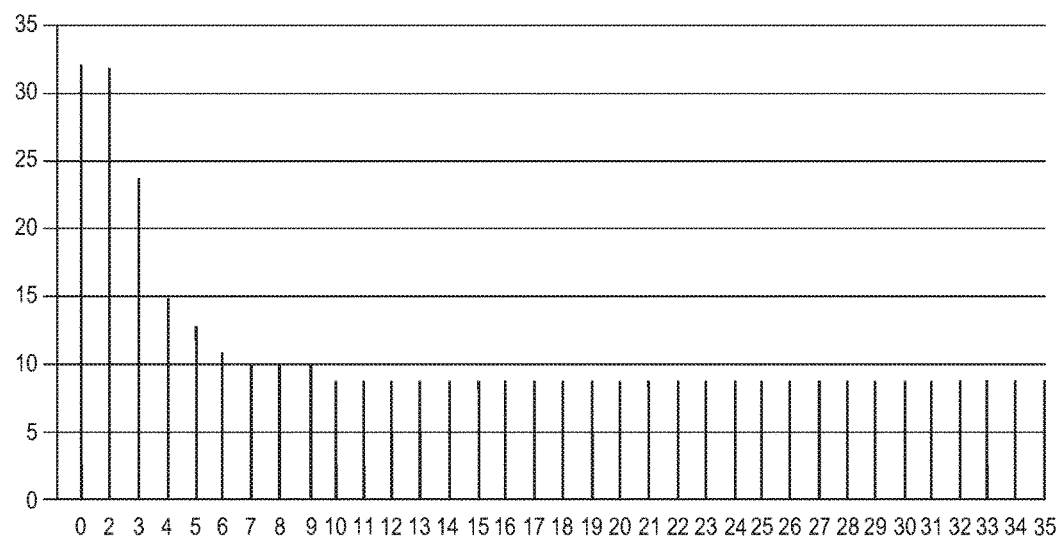
Figure 9B:
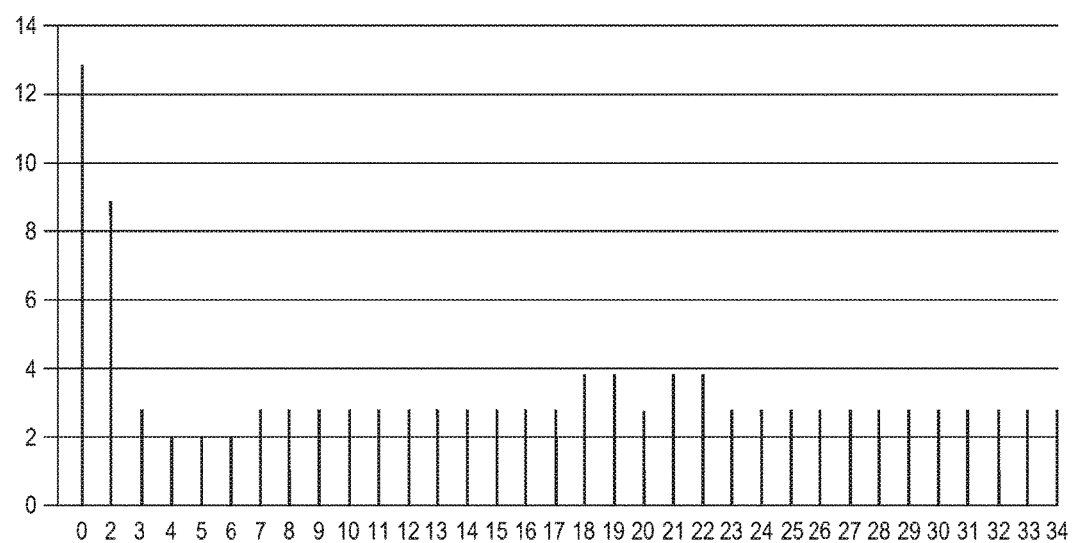
Figure 9C:
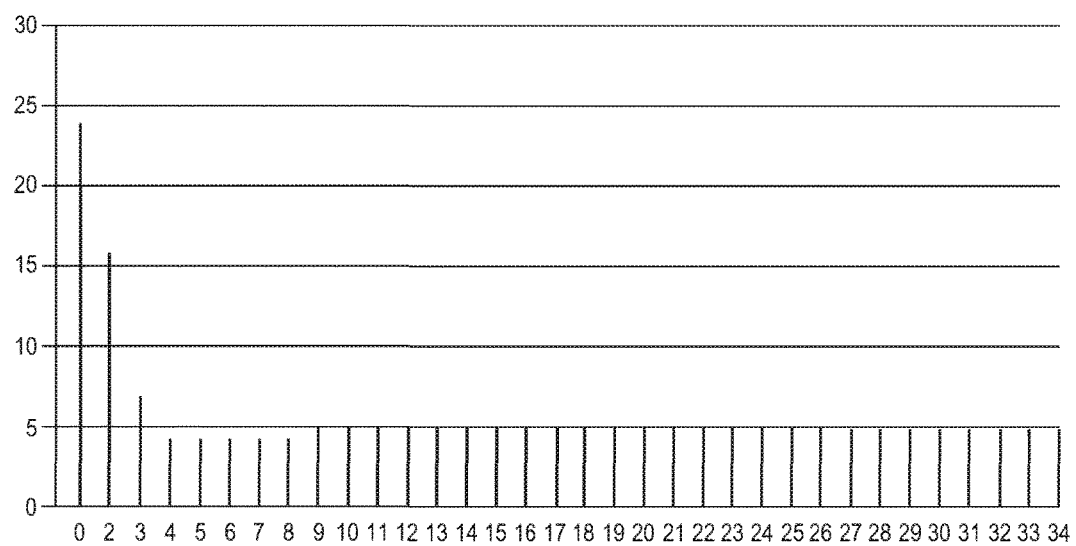

FIGS. 9A, 9B and 9C show figures respectively analogous to FIGS. 8A, 8B and 8C for a sample having a glucose concentration of 19 mM.

DESCRIPTION OF PARTICULAR EMBODIMENTS

Figure 1:
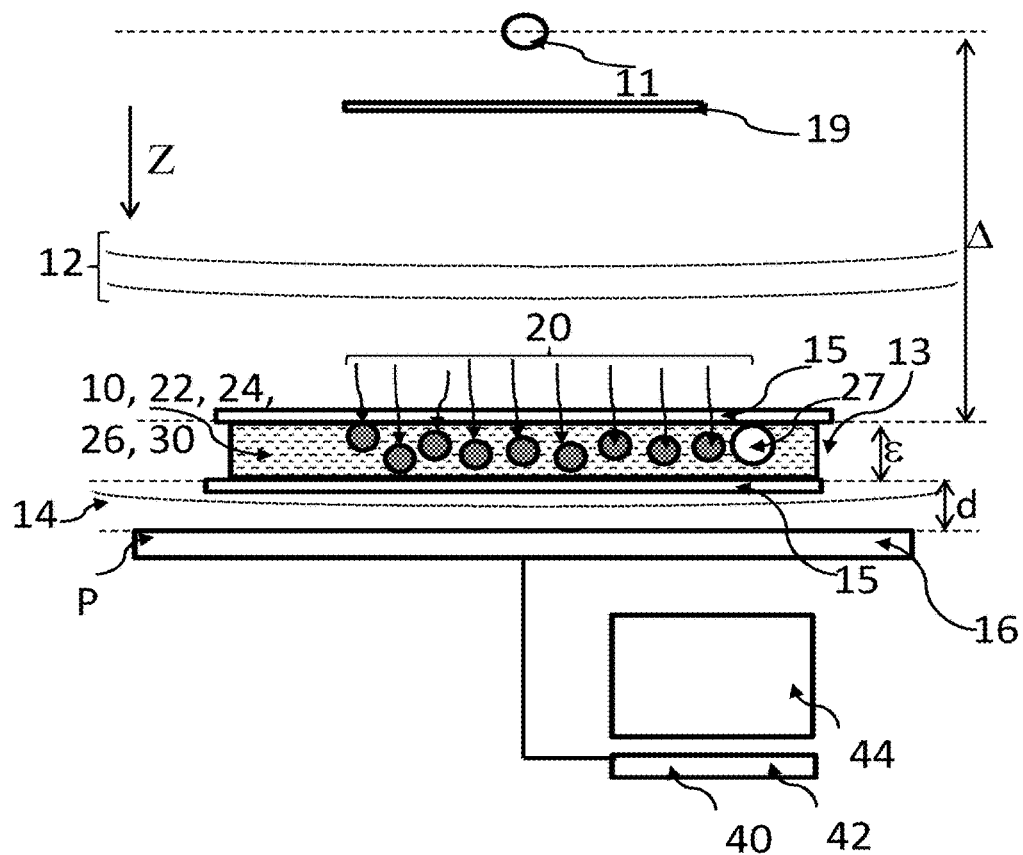
FIG. 1 shows a device allowing the invention to be implemented.

FIG. 1 shows an exemplary device according to the invention. A light source 11 emits light 12, or incident light, in a light spectral band, in the direction of a sample 10, along an axis of propagation Z.

The sample 10 includes a fluid and particles 20 bathing in this fluid. The fluid may especially be a bodily fluid, for example blood. It may especially be whole blood. The particles 20 may be blood particles, and more particularly red blood cells.

The distance Δ between the light source and the sample is preferably larger than 1 cm. It is preferably comprised between 1 and 30 cm and is typically 5 cm.

The light source 11 may be a light-emitting diode or a laser light source, for example a laser diode.

Preferably, the light source may be considered to be point-like, but this is not absolutely necessary. The term point-like means that the diameter (or diagonal) of the source must be smaller than one fifth and better still one tenth of the distance between the sample and the light source. Thus the light 12 impinges the sample in the form of plane waves, or waves that may be considered to be such.

The light source 11 may be associated with a diaphragm 18 (not shown in FIG. 1) so as to appear point-like. The aperture of the diaphragm is typically comprised between 50 µm and 1 mm and preferably between 50 µm and 500 µm. It is not necessary for a diaphragm to be present.

The light source 11 may also be fiber-coupled. In this case, an optical fiber extends between a first end, placed facing a light source, and collecting the light of the latter, and a second end, emitting the light toward the sample. In this case, this second end is considered to be the light source 11.

The light source 11 may include an optical filter 19, especially a band-pass filter, allowing the light spectral band of the light 12 of the light source 11 to be adjusted. The light spectral band of the light emitted by the light source 11 is adapted to an absorption spectrum of a color indicator 24, which is described below.

The sample 10 is contained in a fluidic chamber 13. The sidewalls of the chamber are not shown. The fluidic chamber 13 is for example a microcuvette (commonly used in point of care type devices) into which the sample 10 penetrates by capillary action. In FIG. 1, two transparent longitudinal walls 15 that are separated by a distance of 150 µm have been shown. The distance between these two longitudinal walls 15, along the axis of propagation Z, corresponds to the thickness ε of the sample. The latter typically varies between 20 µm and 1 cm, and is preferably comprised between 50 µm and 500 µm, and for example may be 150 µm.

The sample 10 is placed between the light source 11 and an image sensor 16 able to generate an image I, referred to as a transmission image, of a light beam 14 transmitted by the sample 10. The image sensor extends in a detection plane P preferably parallelly or substantially parallelly to the longitudinal walls 15 of the fluidic chamber 13. The expression substantially parallelly means that the two elements may not be rigorously parallel, an angular tolerance of a few degrees, smaller than 10° or 20°, being acceptable.

The image sensor 16 includes a matrix-array of CCD (Charge Coupled Device) or CMOS (Complementary Metal-Oxide Semiconductor) pixels. Image sensors the inter-pixel pitch of which is smaller than 3 µm are preferred because they allow images to be obtained with a satisfactory spatial resolution.

Preferably, the image sensor comprises a matrix of pixels, above which a transparent protective window is placed. The distance between the matrix of pixels and the protective window generally ranges between a few tens of µm and 150 to 200 µm. Preferably, the detection plane P in which the image sensor extends is perpendicular to the propagation axis Z of the incident light wave 12.

The absence, in this example, of magnifying optics between the image sensor 16 and the sample 10 will be noted. This does not exclude the possible presence of focusing microlenses on each pixel of the image sensor 16. This allows a transmission image of the beam 14 transmitted by the sample to be formed while minimizing the distance between the sample and the image sensor. This allows a particularly simple and compact analyzing device to be used. Thus, in the absence of magnifying optics, the distance d between the sample and the pixels of the image sensor is preferably smaller than 2 cm, or even than 1 cm, preferentially comprised between 50 µm and 2 cm, and preferably comprised between 100 µm and 2 mm.

A processor 40, for example a microprocessor, is configured to process the images I acquired by the image sensor 16. In particular, the processor is a microprocessor connected to a programmable and readable memory 42 in which a sequence of instructions allowing the image-processing and calculating operations described in this description to be carried out is stored. This programmable and readable memory 42 may also contain information allowing the device to be calibrated, as will be discussed below. The processor 40 is connected to a display screen 44.

The sample 10 contains an analyte 30 a quantity or concentration of which is sought. In this example, the analyte is glucose. The principles of detection of glucose within a blood sample, making use of enzyme reactions leading to the formation of a color indicator, are described in U.S. Pat. No. 3,964,974 and U.S. Pat. No. 5,866,349. Generally, this colorimetric method is based on:
  the oxidation of the glucose by NAD (acronym for nicotinamide adenine dinucleotide) in the presence of GDH (acronym for glucose dehydrogenase), leading to the formation of NADH+H+ (acronym for nicotinamide adenine dinucleotide dihydride acid).
  the reduction of a tetrazolium salt by NADH+H+ in the presence of diaphorase (dihydrolipoyl dehydrogenase), reaction leading to the formation of a color indicator 24 the concentration of which is representative of the glucose concentration in the sample.

The tetrazolium salt used may be MTT, acronym for 3-(4,5-dimethylthiazol-2-yl)-2,5-diphenyltetrazolium bromide, in which case the color indicator is formazan and violet in color.

The term color indicator designates a chemical species having a particular color, and the formation of which in the sample is able to modify the absorption spectrum or transmission spectrum of the sample.

Furthermore, the method includes a step of mixing the sample 30 with a first reagent 22, allowing a color indicator 24 to be formed by reaction with the analyte 30 present in the sample. In this example, the analyte is glucose. The first reagent 22 may include GDH, NAD, diaphorase and MTT.

In a sample containing whole blood, the glucose is present in the plasma and in the red blood cells 20 suspended in the plasma. In order to take into account the quantity of glucose within the red blood cells, the method may include a step of hemolysis, a second reagent 26, referred to as the lysis reagent, which is able to lyse the red blood cells, then being added. For example, this second reagent 26 is saponin.

However, the lysis of the red blood cells 20 may lead to air bubbles 27 forming in the sample. Specifically, after mixing with the first and second reagents the sample gradually colors because of the formation of the color indicator 24. However, this coloration is not spatially uniform, in particular because of the presence of air bubbles. Thus, the optical transmittance T of the sample is not uniform.

By optical transmittance, it is meant a comparison of the intensity of a light beam incident on the sample with the intensity of a light beam transmitted by the sample. The comparison may especially be a ratio, in which case:

$$T^\lambda = \frac{I^\lambda}{I_0^\lambda},$$

where:
  $T^\lambda$ is the optical transmittance at the wavelength $\lambda$;
  $I_0^\lambda$ is the intensity of the light beam 12 incident on the sample at the wavelength $\lambda$; and
  $I^\lambda$ is the intensity of the light beam 14 transmitted by the sample at the wavelength $\lambda$.

The formation of the color indicator 24 representative of the analyte 30 leads to a decrease in the optical transmittance in the absorption spectral band (or coloration spectral band) of the indicator.

Figure 2:
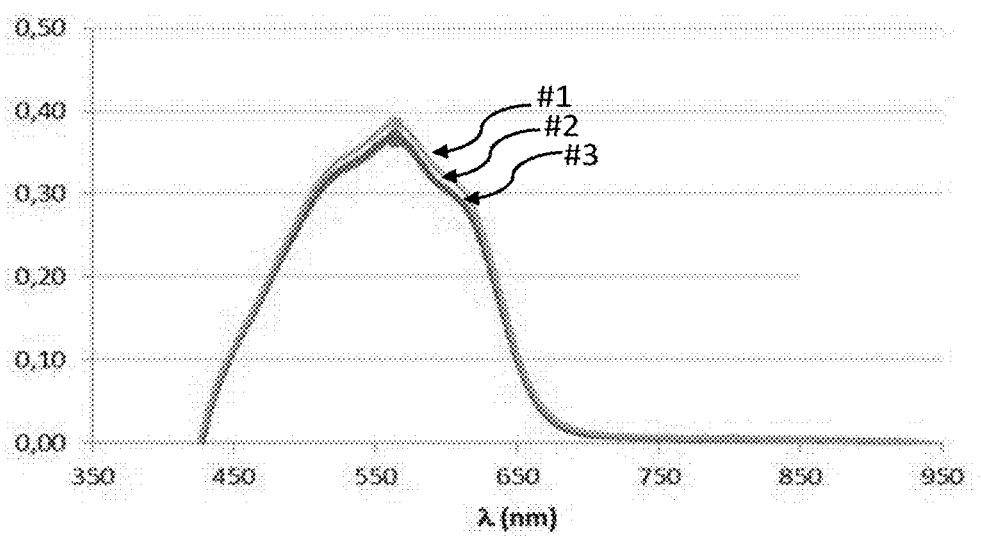
FIG. 2 shows three measurements of the absorption spectrum of a color indicator, in this case Formazan, used in one embodiment.

FIG. 2 shows the absorption spectrum of formazan. It was obtained experimentally by reacting MTT and NADH in the presence of diaphorase in a PBS (Phosphate Buffered Saline) buffer of pH 7.4 at 30° C. The total reaction volume was equal to 300 microliters and the reaction was carried out in a 96-well microplate. After 15 minutes of reaction, a measurement of absorptance DO was carried out using a microplate reader sold by Tecan in order to determine the absorption spectrum of the produced formazan. Thus, when the color indicator 24 implemented in the method is formazan, the absorption spectral band extends between 370 and 670 nm, with an absorption maximum at about $\lambda=565$ nm. FIG. 2 shows three measured spectra, referenced #1, #2 and #3, these three spectra being superposed on one another.

A device similar to the one shown in FIG. 1 was tested using:
  a laser diode from the manufacturer Thorlabs emitting at a wavelength of 650 nm by way of excitation source 11,
  a monochromatic 12-bit CMOS image sensor from the manufacturer Mightex, reference BTN-BO50-U, by way of image sensor 16,
  a microcuvette from Hemocue, reference HE114701, containing the sample and the various reagents required to determine the quantity of glucose.

The microcuvette was placed between the laser diode and the CMOS sensor, at a distance of $\Delta=5$ cm from the laser source and at a distance of d=1 mm from the CMOS sensor. The sample was venous human whole blood sampled on EDTA (ethylenediaminetetraacetic acid), the latter acting as an anticoagulant.

Various trials were carried out by mixing the whole blood with a calibrated amount of glucose, using a glucose solution from the provider Sigma-Aldrich and of reference G8644.

The blood was used to fill the aforementioned microcuvette, by capillary action. This microcuvette firstly contained, in embedded form, a first reagent 22 allowing formazan to be formed depending on the glucose concentration in the sample, this first reagent 22 including GDH, NAD, MTT and diaphorase. The microcuvette secondly contained a second reagent 26 for lysing the red blood cells. In this example, the second reagent 26 is saponin.

Figure 3A:
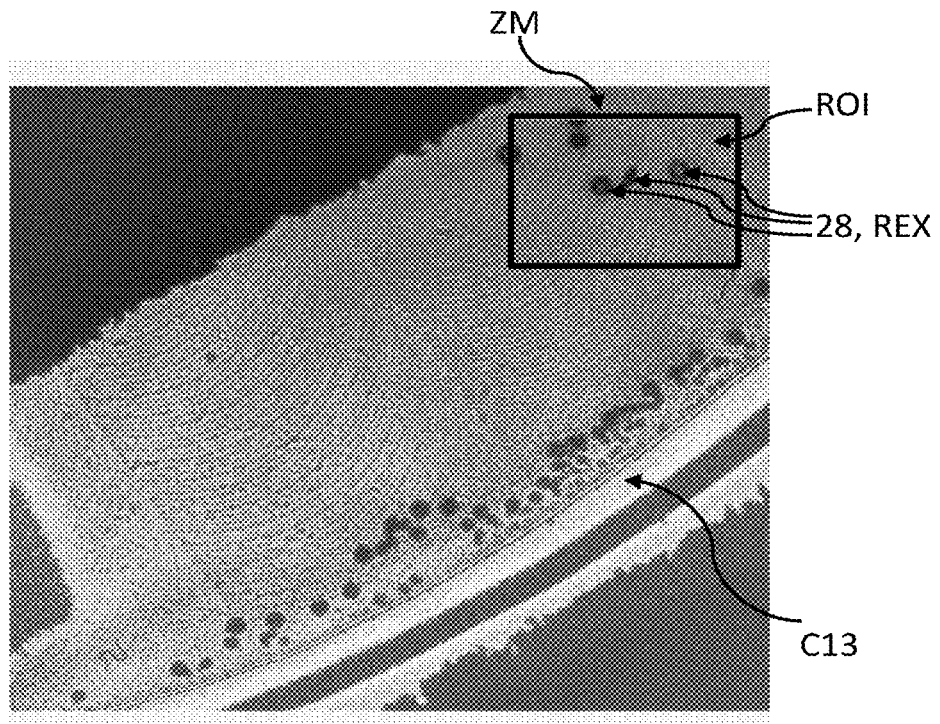
FIGS. 3A and 3B show images obtained in one exemplary embodiment, from a sample comprising whole blood, for two different concentrations of glucose in the sample.
Figure 3B:
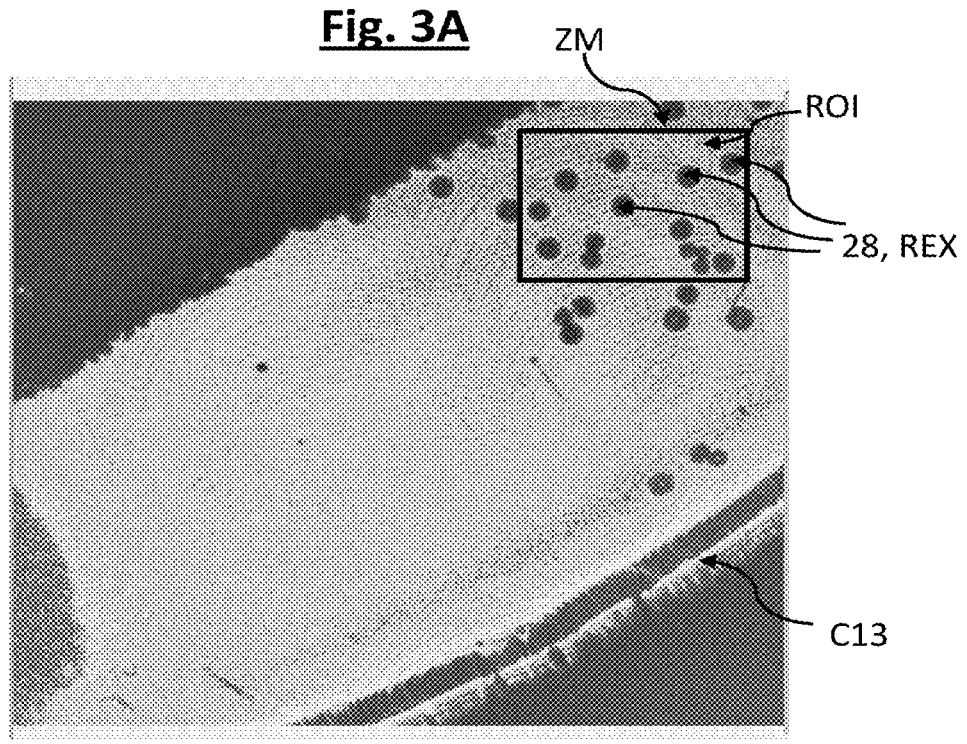

FIGS. 3A and 3B show images obtained by the CMOS sensor when the glucose concentration in the sample is equal to 9.4 and 2.3 mM, respectively. Each image was obtained 120 seconds after the blood had been introduced into the microcuvette, the exposure time being 0.3 ms.

In each figure, the outline C13 of the microcuvette 13 in which the sample lies may be seen. Circular arcs generated by the manufacturing process of the microcuvette may also be seen.

Glucose is quantified in a measuring zone ZM of each transmission image I encompassing 640×460 pixels. This measuring zone ZM is indicated by a rectangle in FIGS. 3A and 3B. The intensity of the light collected by the image sensor depends on the optical transmittance of the analyzed sample. The higher the glucose concentration in the sample, the higher the concentration of formazan formed in the sample and the lower the optical transmittance of the sample, thus decreasing the intensity of the light detected by the image sensor 16.

Thus, the higher the glucose 30 concentration, the darker the image formed by the image sensor. This variation in optical transmittance may be quantified using a quantity k representative of the intensity of the pixels in the measuring zone ZM. This quantity k may be established from the integral or mean of the pixels in this measuring zone. A calibration carried out on calibrating solutions, in which the glucose concentration is known, allows the measured quantity k to be related to the glucose concentration in the sample. The data obtained during this calibration are stored in the memory 42.

However, the lysis of the red blood cells is accompanied by the formation of air bubbles 27 in the sample, the latter appearing in the form of dark disc-shaped traces 28 in each image. The number thereof and their position, in the measuring zone ZM, are random, as FIGS. 3A and 3B show, and vary over time. Thus, the optical transmittance of the sample is not spatially uniform. This nonuniformity may give rise to significant measurement errors.

Thus, it is proposed to establish a quantity representing the intensity of the pixels in the measuring zone ZM while minimizing the impact of air bubbles. To do this, before calculating the quantity k, a region of interest ROI is defined in the measuring zone, this region of interest comprising all the pixels located in the measuring zone other than the pixels corresponding to the traces 28 formed by the air bubbles 27. In other words, inside the measuring zone ZM, a region of interest ROI and at least one region of exclusion REX are defined, the latter being considered to be representative of a trace 28. A measuring zone may include a plurality of regions of exclusion, each corresponding to a trace 28. The region of interest therefore corresponds to a region that is complementary, in the measuring zone, to each region of exclusion. Most often, the measuring zone ZM includes a plurality of regions of exclusion REX, these regions being separate from one another and isolated from one another, in such way that the region of interest extends between these various regions of exclusion. Each region of exclusion is especially bounded by a closed outline, especially of annular, circular or polygonal shape.

The quantity calculated is then dependent on the number of pixels in the region of interest thus defined, but does not take the number of pixels in the region of exclusion REX or regions of exclusion REX present in the measuring zone ZM.

With regard to FIGS. 3A and 3B, in each measuring zone ZM, it is possible to delimit a region of interest ROI that corresponds to said measuring zone minus the regions of exclusion REX, each region of exclusion corresponding to a dark disc. It will be noted that the mean intensity of the pixels in the region of interest shown in FIG. 3A is significantly lower than the mean intensity of the pixels in the region of interest shown in FIG. 3B because the glucose concentration is higher in the sample shown in FIG. 3A, this higher glucose concentration resulting in a lower optical transmittance.

Comparative trials were carried out on samples A, B, C, D and E the glucose concentration of which was respectively equal to 0.4 mM, 2.3 mM, 4.8 mM, 9.4 mM and 19 mM.

Figure 4A:
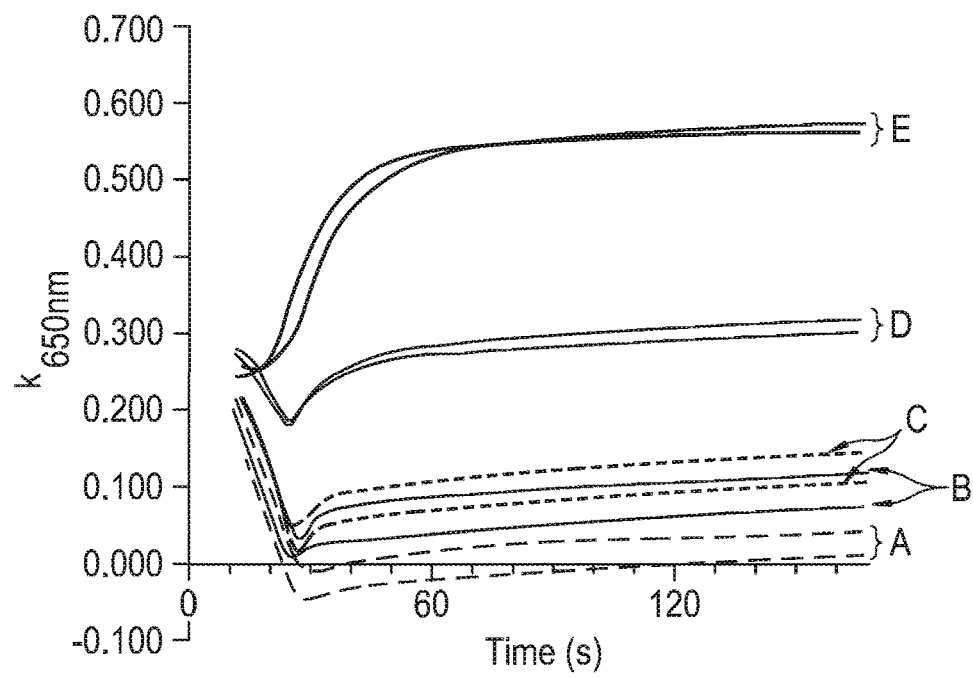
FIGS. 4A and 4B show the results of measurement comparisons.
Figure 4B:
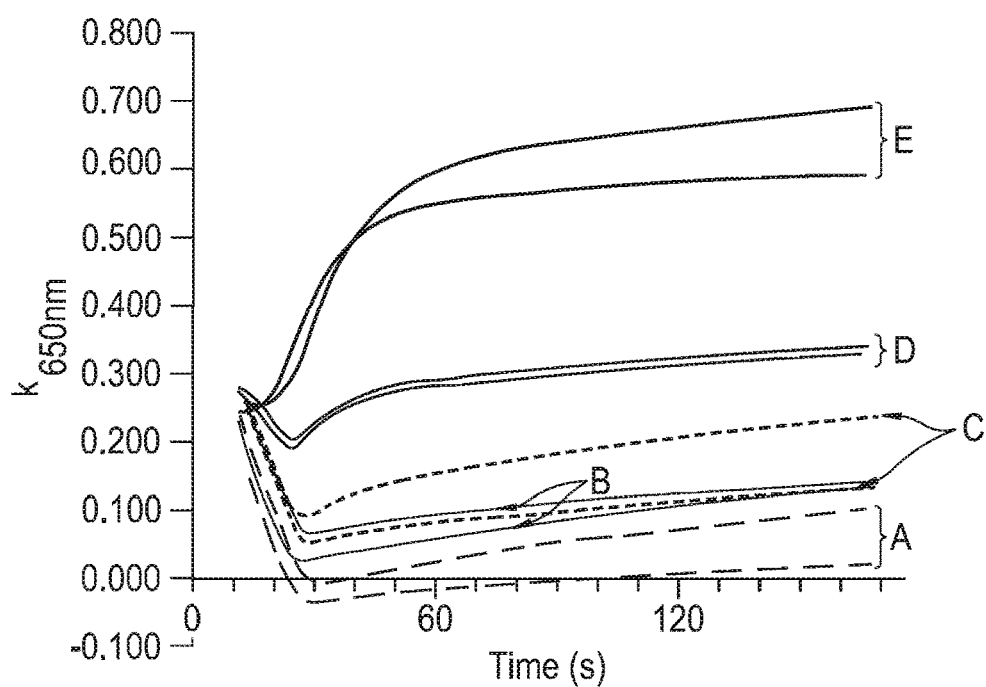

The protocol described with regard to FIGS. 3A and 3B was reproduced on each sample. A quantity representing the intensity of the light transmitted by the sample was determined from an initial time, namely the time the sample penetrated into the fluidic chamber, this time corresponding to the initial time $t=t_0=0$. The quantity was calculated over a period of 170 s after the initial time. FIGS. 4A and 4B show the variation of the quantity as a function of time. It will be noted that:

the quantity k, the variation over time of which is shown in FIG. 4A, corresponds to the mean intensity over the region of interest ROI corresponding to the measuring zone ZM after exclusion of each region of exclusion REX representative of the traces 28. This mean intensity is normalized by the mean intensity, in the measuring zone ZM, of a reference image $I_0$ obtained without a sample between the light source and the image sensor. Because of this normalization, the quantity k corresponds to the mean optical transmittance, such as defined above, in the region of interest ROI.

The quantity k', the variation over time of which is shown in FIG. 4B, corresponds to the mean intensity in the measuring zone ZM. This mean intensity is normalized by the mean intensity, in the measuring zone ZM, of a reference image $I_0$ obtained without a sample between the light source and the image sensor. Because of this normalization, the quantity k' corresponds to the mean of the optical transmittance, such as defined above, in the measuring zone region ZM.

In this example, the region of interest is obtained by thresholding of the intensities of the pixels in the measuring zone. Pixels the intensity of which exceeds a certain threshold are considered to belong to the region of interest ROI, the others being considered to belong to a region of exclusion.

In other words, the quantity represented in FIG. 4A may be expressed in the form:

$$k = \frac{\frac{\sum_{r \in ROI} I(r)}{N_{r \in ROI}}}{\frac{\sum_{r \in ZM} I_0(r)}{N_{r \in ZM}}}$$

where:
r is the position of a pixel in the image I;
I(r) is the intensity of the pixel r of the image I;
$I_0(r)$ is the intensity of the pixel r of the reference image $I_0$; and
$N_{r \in ROI}$ is the number of pixels contained in the region of interest ROI.

The quantity shown in FIG. 4B may be expressed in the form:

$$k' = \frac{\frac{\sum_{r \in ZM} I(r)}{N_{r \in ZM \geq P}}}{\frac{\sum_{r \in ZM} I_0(r)}{N_{r \in ZM}}}$$

where:
$N_{r \in ZM}$ designates the number of pixels contained in the measuring zone ZM.

Comparison of FIGS. 4A and 4B shows that the quantity k is preferable to the quantity k'. Specifically, the quantity k', the variation over time of which is shown in FIG. 4B, varies constantly over time, and may take substantially different values for a given quantity of analyte. This is especially the case for samples A, B and E that have a glucose concentration of 0.4 mM, 4.8 mM and 19 mM, respectively. In contrast, the quantity k, the variation over time of which is shown in FIG. 4A, appears more reliable: its variation as a function of time is less marked, beyond a time of 60 s after the initial time. In addition, measurements corresponding to a given glucose concentration are more repeatable.

It will be understood that acquiring an image, and not a spatially unresolved one-dimensional optical signal as in the prior art, makes it possible to identify the traces 28 and to exclude them from the estimation of glucose concentration. This makes it possible to obtain a more reliable estimation of the amount of glucose in the blood, because the traces 28, which are not representative of the observed coloration, are not taken into account in the portion of the image analyzed. Moreover, in addition to the traces related to the air bubbles produced by the hemolysis, obtaining an image I allows any other perturbation, for example a manufacturing defect in a fluidic chamber 13, or even a dust particle inside or outside this chamber, to be excluded.

It will also be noted that a second light source illuminating the sample at a wavelength of 880 nm is not required.

Thus, on the basis of an image acquired by the image sensor, and using a single light source, it is possible to estimate the glucose content of a blood sample, and, more generally, to determine the quantity of an analyte present in a fluid sample, by observing a coloration of the sample resulting from a reaction of this analyte.

In this example, the region of interest ROI is determined by image thresholding, the pixels belonging to the region of interest when their intensity is higher than a threshold. The value of this threshold was set equal to 50 for samples A, B and C, 30 for the sample D and 20 for the sample E.

This threshold may be preset; it may also be defined, case-by-case, on the basis of each image, for example by analysis of a histogram of the measuring zone ZM. Specifically, the pixels corresponding to a region of exclusion form a peak in the histogram; the threshold may be determined on the basis of an intensity determined from this peak, for example a limit of this peak, especially the upper limit when a region of exclusion appears in the form of a dark trace.

Other methods for determining the region of interest ROI, based on known image segmentation and morphology analysis techniques, are envisionable. Advantage is then taken of the fact that each region of exclusion REX corresponds to a substantially circular closed shape. Shape or outline recognition algorithms may therefore be implemented to identify and delimit each region of exclusion.

Figure 5:
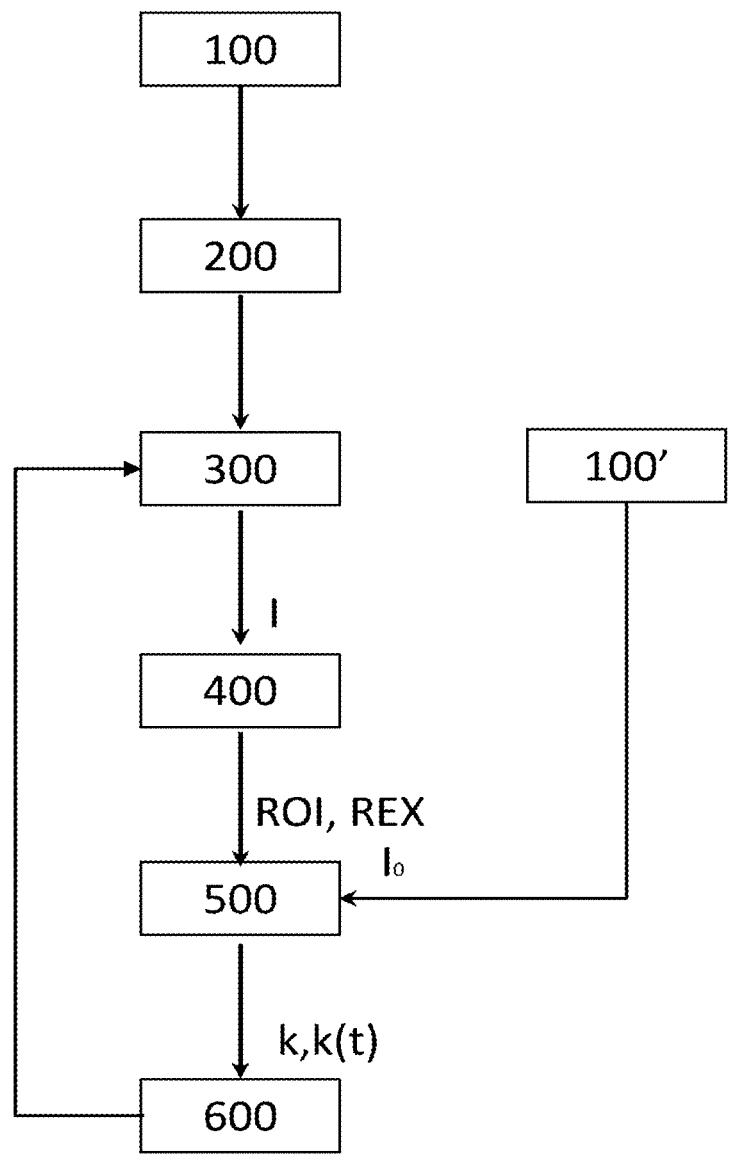
FIG. 5 shows the main steps of one embodiment of a method according to the invention.

FIG. 5 summarizes the main steps of a method for estimating glucose concentration according to the invention.

In a step 100, the bodily fluid is introduced into a fluidic chamber 13. The fluid introduced into the chamber forms the sample 10 to be analyzed.

In a step 200, the fluid is mixed with a first reagent 22 able to form a color indicator 24 in the presence of glucose 30, and a second reagent 26 able to lyse the red blood cells present in the sample. The first and second reagents may especially be present in said fluidic chamber in the dry state, for example in lyophilized form.

In a step 300, the fluidic chamber is illuminated by a light source 11 and the light 14 transmitted by the sample is collected by an image sensor 16 so as to form a transmission image I therefrom. This transmission image may be formed after a preset time period T following the introduction of the sample into the fluidic chamber.

In a step 400, the transmission image I is analyzed so as to determine, in a measuring zone ZM of said image, a region of interest ROI and one or more regions of exclusion (REX).

In a step 500, a quantity k representative of the intensity of the pixels in the region of interest at the time T is calculated from the transmission image I, the pixels of each region of exclusion not being taken into account in the calculation of the quantity k.

In a step 600, the quantity k is compared to calibrated quantities, obtained from calibrated solutions under analogous experimental conditions, so as to estimate the amount or concentration of the analyte 30. The calibrated quantities are stored in a memory 42 that is connected to the processor 40.

The step 500 may require an image $I_0$, referred to as an initial image, formed by the image sensor when there is no fluid in the fluidic chamber, or when there is no fluidic chamber, to be acquired. This reference image $I_0$ may be established in a step 100' when there is no fluidic chamber between the light source 11 and the image sensor 16, before or after formation of the image I. It may also be established by placing a fluidic chamber empty of sample between the light source 11 and the image sensor 16.

The steps 100 and 200 may be inverted or carried out simultaneously.

Alternatively, steps 300 to 600 are repeated at various times and, in step 600, a plurality of quantities k are determined as a function of time t, the amount or concentration of analyte then being estimated from the variation k(t) of said quantity over time.

According to another embodiment, the light source 11 and the image sensor 16 are placed on the same side relative to the sample 10. The image sensor then detects an image I' of the light 14' reflected and possibly backscattered by the sample. The formation of a color indicator 24 modifies the optical absorption properties $A_\lambda$ of the sample, especially in the absorption spectral band of the color indicator 24. It will be noted that the optical absorptance, at a given wavelength $\lambda$, may be defined by the expression: $A^\lambda = 1 - T^\lambda$, $T^\lambda$ being the optical transmittance defined above.

The advantage of this embodiment is that it may be applied to thicker samples, for example the thickness of which exceeds 5 mm or even 1 cm.

According to one variant of the embodiment described above, prior to implementing the step 400, it is sought to ensure that the lysis of the red blood cells is advanced enough for the image analyzed in the following steps not to be influenced by the scattering of light 12 by these red blood cells. In other words, a time $T_l$, referred to as the lysis time, beyond which the lysis may be considered to have completed, is waited.

Specifically, until the lysis has reached a sufficiently advanced stage, scattering by the red blood cells in the sample influences the measurement of transmitted light 14. This may cause a measurement error. To guard against this, it is preferable to wait until the lysis has completed, or until it is advanced enough for the transmission of light through the sample to be representative of the optical absorptance of the sample, the influence of the scattering then being negligible because of the small residual amount of red blood cells.

Figure 6:
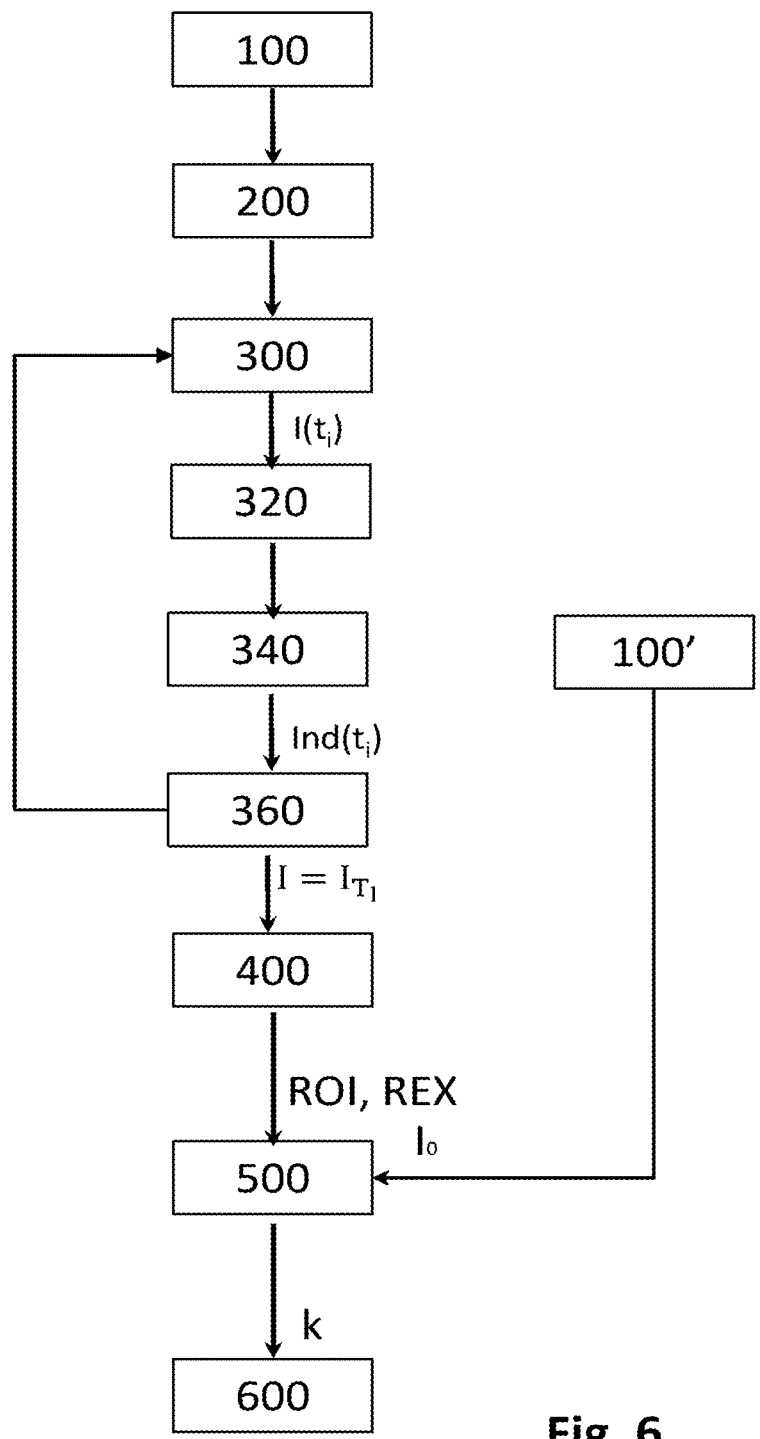
FIG. 6 shows the steps of a variant of this embodiment.

This variant is shown in FIG. 6. In a step 300, the fluidic chamber is illuminated by the light source 11 and the light 14 transmitted by the sample is collected by an image sensor so as to form a transmission image $I(t_i)$ acquired at the time $t_i$. The variable $t_i$ is a temporal variable representing a sampled time.

In a step 320, a lysis inspection zone ZC is determined in the image $I(t_i)$. This inspection zone corresponds to all or some of the analyzed fluid sample in the fluidic chamber.

In a step 340, a lysis indicator $Ind(t_i)$ is established, said indicator being determined using the intensity of the pixels in the lysis inspection zone. This lysis indicator is for example the variance or standard deviation of the distribution of the intensity of these pixels.

In a step 360, a lysis level is determined from the value of the indicator $Ind(t_i)$. Depending on its value, it is either concluded that the lysis is sufficiently advanced, or steps 300 to 360 are reiterated with an image $I(t_{i+1})$ acquired at a time $t_{i+1}$ subsequent to the time $t_i$. When the value of the lysis indicator has met a certain criterion, called the lysis criterion, a lysis end time $T_l$ is considered to have been reached and the following steps 400 to 600 are carried out either with another image being acquired, or on the basis of the image $I(t=T_l)$ acquired at the time $T_l$.

The lysis indicator may be established image by image, one lysis indicator $Ind(t_i)$ being associated with each image $I(t_i)$.

It may also be representative of a correlation or a difference between two successive images $I(t_i)$ and $I(t_{i-1})$, one indicator $Ind(t_i)$ being attributed to the pair of images $I(t_i)$, $I(t_{i-1})$. In this case, in the step 340 a difference image $\Delta(t_i)$ such that $\Delta(t_i)=I(t_i)-I(t_{i-1})$ is determined, for example. This image $\Delta(t_i)$ is referred to as the comparison image at the time $t_i$. The lysis indicator $Ind(t_i)$ may correspond to the mean or standard deviation, or even the variance of said comparison image $\Delta(t_i)$.

The lysis end criterion is determined depending on the variation of the lysis indicator $Ind(t_i)$ over time. In particular, the lysis end criterion is considered to have been reached when the lysis indicator no longer varies significantly. The lysis end criterion may also be a preset threshold value, the lysis end time $T_l$ being considered to have been reached when the lysis indicator $Ind(t_i)$ crosses such a threshold.

The other steps 100, 200, 400, 500, 600 are analogous to the steps described with regard to FIG. 5. The inspection zone ZC defined in step 320 may be similar to the measuring zone ZM described with respect to step 400.

Experimental trials were carried out in order to determine a lysis end time $T_l$ by image analysis, under various conditions.

The images in FIGS. 7A, 7B, 7C, 7D and 7E show a sample similar to that shown in FIGS. 3A and 3B, the glucose concentration being 4.8 mM. An inspection zone ZC of 640×480 pixels was selected. This zone is represented by a white rectangle in the image 7A and it is identical in all the images 7A to 7E. If t0 designates the introduction of the sample into the microcuvette, these images were acquired at $t_0+10$ s, $t_0+20$ s, $t_0+30$ s, $t_0+60$ s and $t_0+120$ s, respectively.

Figure 7A:
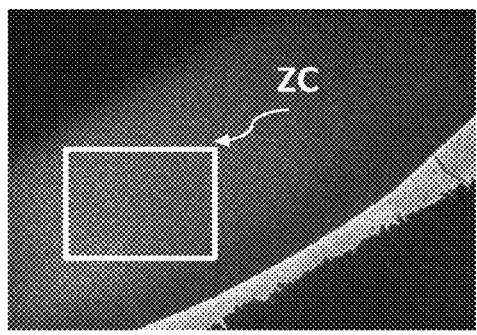
FIGS. 7A, 7B, 7C, 7D and 7E show images of the sample at various times (10 s, 20 s, 30 s, 60 s and 120 s, respectively) after the sample has been introduced into a microfluidic chamber, the sample having a glucose concentration equal to 4.8 mM.
Figure 7B:
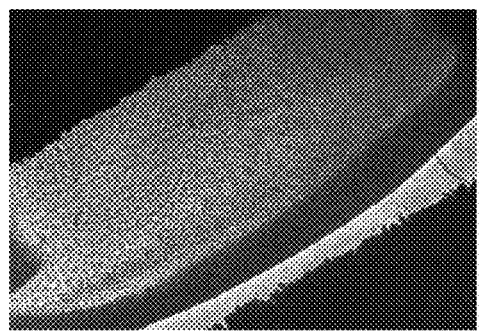
Figure 7C:
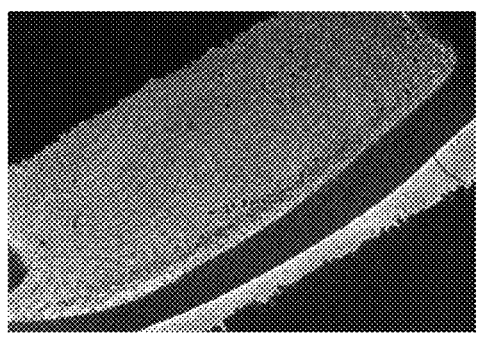
Figure 7D:
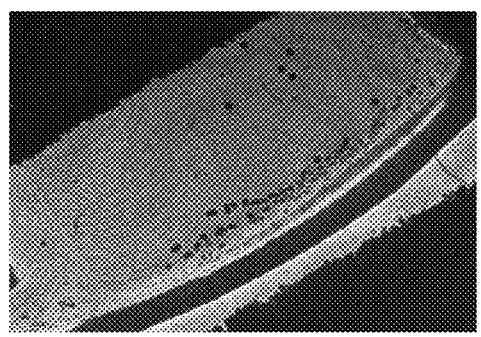
Figure 7E:
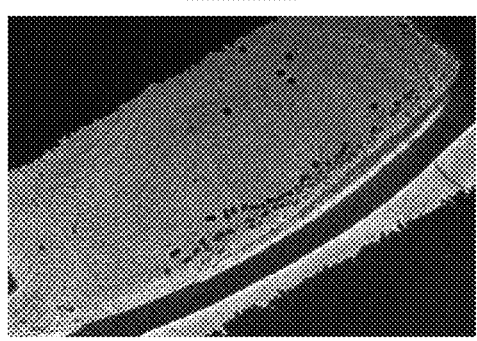

It will be noted that at $t_0+10$ s (FIG. 7A), the image appears noisy, especially in comparison with the other images, this noise being due to the scattering of the incident light by red blood cells. It will be understood that the signal measured by the image sensor is greatly influenced by the scattering. As the amount of time passed since the introduction increases, the images are less and less noisy, and this is particularly clear between $t_0+10$ s (FIG. 7A) and $t_0+30$ s (FIG. 7C). Beyond $t_0+30$ s, bubbles are observed to form, the bubbles appearing in the form of black discs the area of which increases over time. This increase in area may in particular be appreciated by comparing FIGS. 7C to 7E. The inventors consider that the lysis may be considered to be complete, or to no longer be changing significantly, after $t_0+30$ s.

Figure 7F:
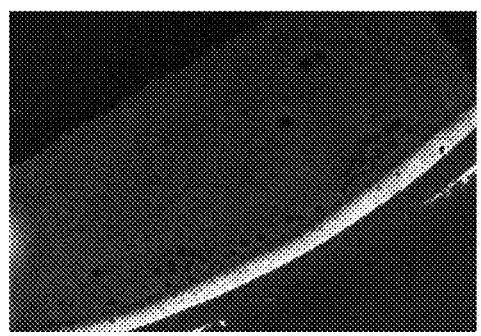
FIG. 7F shows the image of a sample 120 s after it has been introduced into a microfluidic chamber, the sample having a glucose concentration equal to 19 mM.

FIG. 7F shows a sample the glucose concentration of which is 19 mM, the image being acquired at $t_0+120$ s. It may be seen that the grey level is much darker than in the image 7E, which was produced under the same conditions with a lower glucose content. This is due to the fact that the intensity of the transmitted light beam is almost entirely governed by absorption due to the color indicator, the concentration of the latter being higher in FIG. 7F than in FIG. 7E because of the difference in the amount of glucose.

FIG. 8A shows the variation in the standard deviation of the intensity of the pixels in the lysis inspection zone ZC as a function of time. More precisely, the x-axis represents the incrementation number of each analyzed image, the time interval between each image being 5 seconds. Image 1 corresponds to $t_0+10$ s, image 2 corresponds to $t_0+15$ s, etc. The lysis inspection zone ZC is the same in each image, and corresponds to that shown in FIG. 7A.

The standard deviation fluctuates in the first images, then stabilizes from the image i=5, corresponding to a time of 30 seconds after the introduction of the sample into the microcuvette 30. From this time, the lysis is considered to have completed, or at least to be advanced enough for the measurements not to be significantly affected by scattering. Thus, the standard deviation of each image may constitute a lysis indicator.

FIG. 8B shows the variation in the mean, in the lysis inspection zone, determined from comparison images $\Delta(t_i)$, each comparison image being obtained, in this example, by subtracting an image $I(t_i)$ acquired at a time $t_i$ from an image $I(t_{i-1})$ acquired at a time $t_{i-1}$. Just as in the example described with regard to FIG. 8A, this figure was produced from images acquired in succession every 5 s, image 1 corresponding to $t_0+10$ s. The x-axis represents the number i of each analyzed comparison image $\Delta(t_i)$, the time interval between each image being 5 seconds. The y-axis represents the average value of the intensity of the pixels in the lysis inspection zone ZC of each comparison image $\Delta(t_i)$. The mean value is observed to stabilize from the comparison image corresponding to the index i=4, i.e. $t_0+25$ s. Thus, the mean of the intensity of the pixels of comparison images $\Delta(t_i)$ acquired at different times $t_i$ may constitute a lysis indicator.

FIG. 8C shows the variation in the standard deviation, in the lysis inspection zone ZC, determined from the comparison images $\Delta(t_i)$ described with regard to FIG. 8B. The standard deviation is observed to stabilize from the image corresponding to the index i=4, i.e. $t_0+25$ s. Thus, the standard deviation of the intensity of the pixels of comparison images $\Delta(t_i)$ acquired at different times $t_i$ may constitute a lysis indicator.

FIGS. 9A, 9B and 9C respectively show results obtained in the same way as those shown in FIGS. 8A, 8B and 8C. These figures were obtained using a sample the glucose concentration of which was 19 mM.

Just as in FIGS. 8A, 8B and 8C, and generally, the lysis indicator allows a lysis end time to be determined from which the lysis of the particles in the sample is sufficiently advanced that the image acquired by the image sensor is not or not greatly influenced by the scattering of light 12 by the particles. From this time, the image is mainly influenced by the absorption of light 12 by the sample. In the above discussed examples, this time is about 25 to 30 seconds after the introduction of the sample into the microcuvette.

This time, called the lysis time, is reached when the lysis indicator meets a certain criterion called the lysis criterion. The lysis criterion may be a threshold value of the indicator. It may also be a value representing a stabilization in the variation over time of the indicator, determined on the basis of a comparison of indicators established using a plurality of consecutive images. The term comparison may designate a subtraction or a ratio.

Thus, another object of the invention is a method for determining a lysis indicator in a fluid sample, the sample containing particles, the method including mixing the sample with a lysis reagent able to lyse said particles, the method including the following steps:

illuminating said sample 10 using a light source 11 configured to emit light 12 toward the sample, acquiring, using an image sensor 16, an image I of light transmitted or reflected by the sample, and determining a lysis indicator from said image.

This lysis indicator represents a state of advancement of the lysis of the particles in the sample, under the effect of the lysis reagent. When this lysis indicator meets a certain criterion called the lysis criterion, most of the particles may be considered to have been lyzed. The effect of scattering of light by the sample is then negligible. The image acquired by the detector is then representative of the absorption of the light transmitted or reflected by the sample.

The lysis indicator may comprise:

a term representing the dispersion of the intensity of the pixels of an image acquired by the image sensor about a mean value, for example a variance or a standard deviation of this image;

a comparison, for example taking the form of a difference or a correlation factor, established between two images acquired at different times $t_i$ and $t_{i-1}$;

a term representing a mean value of a comparison image $\Delta(t_i)$ resulting from such a comparison, or representing a dispersion about this mean value, for example a variance or a standard deviation of this comparison image.

The method described above, applied to the determination of a glucose concentration in total blood, may be generalized to any analyte present in a fluid sample, in particular a bodily sample.

The invention claimed is:

1. A method for estimating an amount of an analyte in a bodily fluid sample containing particles which is in a holder outside a body, comprising:
   a) mixing the sample with a first reagent able to form a color indicator in the presence of said analyte,
   b) following this mixing, illuminating the sample using a light source able to emit light toward the sample,
   c) acquiring, using an image sensor, an image of light transmitted or reflected by the sample, and
   d) estimating, depending on said image, an amount of said analyte, by:
      i) selecting a measuring zone in said image, said measuring zone comprising a plurality of pixels,
      ii) determining, inside the measuring zone, a region of interest and at least one region of exclusion corresponding to a trace of air bubbles, and
      iii) estimating the amount of analyte from a quantity representative of the intensity of the pixels in said region of interest, without taking into account the intensity of the pixels of each region of exclusion,
   the method also including mixing the sample with a lysis reagent able to lyse said particles resulting in formation of the air bubbles.

2. The method of claim 1, wherein ii) comprises determining at least one region of exclusion, said region of interest corresponding to a portion of said measuring zone not including each region of exclusion thus determined.

3. The method of claim 1, further comprising in d),
   determining a lysis indicator from the image acquired in c),
   estimating the amount of analyte being carried out when this lysis indicator meets a preset lysis criterion.

4. The method of claim 3, wherein when the lysis indicator does not meet said lysis criterion, c) is repeated in such a way that a plurality of lysis indicators are determined from images acquired at various times.

5. The method of claim 4, wherein each lysis indicator is determined by forming a comparative image representing a comparison between two images acquired at various times.

6. The method of claim 1, comprising introducing the sample into a fluidic chamber, c) and d) being performed from a preset time after said introduction.

7. The method of claim 1, comprising acquiring a plurality of successive images of the light transmitted or reflected by the sample, the amount of analyte being determined, in d), depending on the variation in the intensity of each image as a function of time.

8. The method of claim 1, wherein, in d), said quantity representative of the intensity of the pixels in said region of interest includes the integral or mean of the pixels in said region of interest.

9. The method of claim 1, wherein the region of exclusion is determined by thresholding said image or by segmenting said image.

10. The method of claim 1, wherein said particles are red blood cells.

11. The method of claim 1, wherein the analyte is glucose.

12. The method of claim 1, wherein the image sensor is located at a distance from the sample smaller than 1 cm.

13. The method of claim 1, wherein there are no magnifying optics between the sample and the image sensor.

14. The method of claim 1, wherein the sample is placed between said light source and said image sensor, in such a way that the image sensor detects radiation transmitted by the sample to obtain a transmitted image.

15. The method of claim 1, wherein the sample is placed facing said light source and said image sensor, in such a way that the image sensor detects radiation reflected or backscattered by the sample to obtain a reflected image.

16. A device for estimating the amount of an analyte in a fluid sample, the device comprising:
   a light source for emitting light in the direction of said sample,
   a holder for holding the sample between said light source and an image sensor,
   the image sensor being arranged to acquire an image of the radiation transmitted or reflected by the sample when the sample is exposed to said light, and
   a processor able to estimate an amount of analyte in the sample, said processor being configured to implement d) of claim 1.

17. The device of claim 16, wherein the image sensor is located at a distance from the sample smaller than 1 cm.

18. The device of claim 16, wherein there are no magnifying optics between the sample and the image sensor.

19. A method for estimating an amount of glucose in a bodily fluid sample containing red blood cells which is in a holder outside a body, comprising:
   e) mixing the sample with a first reagent able to form a color indicator in the presence of glucose,
   f) following this mixing, illuminating the sample using a light source able to emit light toward the sample,
   g) acquiring, using an image sensor, an image of light transmitted or reflected by the sample, and
   h) estimating, depending on said image, an amount of glucose, by:
      iv) selecting a measuring zone in said image, said measuring zone comprising a plurality of pixels,
      v) determining, inside the measuring zone, a region of interest and at least one region of exclusion corresponding to a trace of air bubbles, and
      vi) estimating the amount of glucose from a quantity representative of the intensity of the pixels in said region of interest, without taking into account the intensity of the pixels of each region of exclusion,
the method also including mixing the sample with a lysis reagent able to lyse said red blood cells resulting in formation of the air bubbles.

* * * * *

UNITED STATES PATENT AND TRADEMARK OFFICE
CERTIFICATE OF CORRECTION

PATENT NO. : 10,049,453 B2
APPLICATION NO. : 15/204300
DATED : August 14, 2018
INVENTOR(S) : Jean-Guillaume Coutard et al.

Page 1 of 1

It is certified that error appears in the above-identified patent and that said Letters Patent is hereby corrected as shown below:

On the Title Page

Item (71) the Applicant's information is incorrect. Item (71) should read:
--(71) Applicants: COMMISSARIAT A L'ENERGIE ATOMIQUE ET AUX ENERGIES ALTERNATIVES, Paris (FR)
AVALUN, Grenoble (FR)--

Signed and Sealed this
Eleventh Day of June, 2019

Andrei Iancu
*Director of the United States Patent and Trademark Office*